United States Patent

Swaisgood et al.

[11] Patent Number: 5,292,372
[45] Date of Patent: Mar. 8, 1994

[54] METHOD OF REMOVING CONTAMINANTS FROM A CONTACT LENS USING ELECTROBLOTTING

[75] Inventors: Harold E. Swaisgood; Marie K. Walsh, both of Raleigh, N.C.

[73] Assignee: North Carolina State University, Raleigh, N.C.

[21] Appl. No.: 942,561

[22] Filed: Sep. 9, 1992

[51] Int. Cl.⁵ .............................................. B08B 6/00
[52] U.S. Cl. .......................................... 134/1; 134/42
[58] Field of Search ................. 134/1, 42; 204/182.7; 422/22

[56] References Cited

U.S. PATENT DOCUMENTS

| | | | |
|---|---|---|---|
| 4,589,965 | 5/1986 | Kreisher | 204/182.8 |
| 4,607,652 | 8/1986 | Yung | 134/184 |
| 4,732,185 | 3/1988 | Cowle et al. | 134/84 |
| 4,836,859 | 6/1989 | Konishi et al. | 134/1 |
| 4,872,965 | 10/1989 | Pankow | 204/299 R |
| 4,921,544 | 5/1990 | Cowle et al. | 134/1 |
| 4,959,133 | 9/1990 | Adcock | 204/182.8 |
| 4,994,166 | 2/1991 | Fernwood et al. | 204/299 R |
| 5,013,420 | 5/1991 | Schuette | 204/299 R |
| 5,037,484 | 8/1991 | Su et al. | 134/7 |
| 5,089,111 | 2/1992 | Zhu et al. | 204/180.1 |
| 5,135,623 | 8/1992 | Dziabo et al. | 134/1 |

Primary Examiner—Mark L. Bell
Assistant Examiner—Thomas G. Dunn, Jr.
Attorney, Agent, or Firm—Bell, Seltzer, Park & Gibson

[57] ABSTRACT

A method of cleaning contaminants from a contact lens is disclosed. The method comprises the steps of positioning a contact lens and an adsorbent so that the adsorbent is disposed between the contact lens and an electric current source, immersing the contact lens, the adsorbent, and the current source in a saline solution, then applying an electric current from the current source through the adsorbent and the contact lens so that contaminants carried by the contact lens migrate to the adsorbent. Additionally, a disposable, arcuate-shaped adsorbent article conformable to and matable with the convex and concave surfaces of the contact lens is also disclosed.

20 Claims, 1 Drawing Sheet

METHOD OF REMOVING CONTAMINANTS FROM A CONTACT LENS USING ELECTROBLOTTING

FIELD OF THE INVENTION

This invention relates generally to the cleansing of contact lenses, and relates more specifically to the cleansing of contact lenses through electroblotting.

BACKGROUND OF THE INVENTION

Perhaps the most common impediment to wearer comfort and visual acuity of contact lenses is the presence of contaminants on the surface of the lens. The large majority of these contaminants are proteins produced by the eye, tear duct, and eyelid for lubrication and protection of delicate optic tissues. The proteins will agglomerate on the surfaces and the interior of the lens to form microscopic protrusions which rub against the cornea and eyelid, thereby causing irritation, inflammation, and discomfort.

There are a number of known methods for removing protein contaminants from a contact lens surface. Some removal systems use a mild detergent to wash the agglomerated proteins from the lens surface; however, these detergents can damage the lens. Others utilize a solution containing a proteolytic enzyme which digests the protein molecules, but this method has proven inadequate for complete protein removal.

One recently conceived solution for removal of protein from contact lenses is the application of electrophoresis techniques. Cowle et al., U.S. Pat. No. 4,921,544, discloses a method wherein the contact lens is placed in an electrophoretic solution within a container, then an electric field is applied to the solution through two electrodes in the solution which causes charged protein molecules attached to the lens to migrate to the oppositely charged electrode. Although the application of electrophoresis to the cleaning of lenses is promising, any protein migrating to an electrode must also overcome a diffusion gradient created by the migration which tends to drive protein from the electrode into solution. An equilibrium is eventually reached, at which point it becomes difficult to further remove protein from the solution at the electrode; some of this free protein then is able to return to the lens.

Another electrochemical solution is offered in Pankow, U.S. Pat. No. 4,872,965. In this method, electrodes are immersed in solution baths external to the lens; current is provided to the lens by a transmission means which rests on the lens surface. Application of electrical current causes contaminants to migrate from the center of the lens to its surface. From this point the contaminants are removed from either the lens surface or from the electrochemical transmission means by an additional wiping step.

Accordingly, it is an object of the present invention to provide an electroblotting method of cleaning contact lenses which overcomes the problem associated with the equilibrium of electrochemical and diffusion gradients. It is a further object of the present invention to provide an electroblotting method of cleaning contact lenses which eliminates the need for wiping protein from the lens after the application of electric current. It is an additional object of the invention to do so with a simple, inexpensive, and easily used method suitable for commercial production.

SUMMARY OF THE INVENTION

These objects and others are satisfied by the present invention, which as a first aspect comprises a method of cleaning contaminants from a contact lens. The method comprises the steps of positioning a contact lens and an adsorbent so that the adsorbent is disposed between the contact lens and an electric current source, immersing the contact lens, the adsorbent, and the current source so disposed in a saline solution, then applying an electric current from the current source through the adsorbent and the contact lens so that contaminants carried by the contact lens migrate to the adsorbent. Preferably, the adsorbent comprises a disposable, arcuate-shaped article conformable to and matable with the convex and concave surfaces of the contact lens.

A second aspect of the present invention is an arcuate-shaped adsorbent article of the type described above. A preferred embodiment of said article is formed of nitrocellulose membrane.

DETAILED DESCRIPTION OF THE INVENTION

Figure 1:
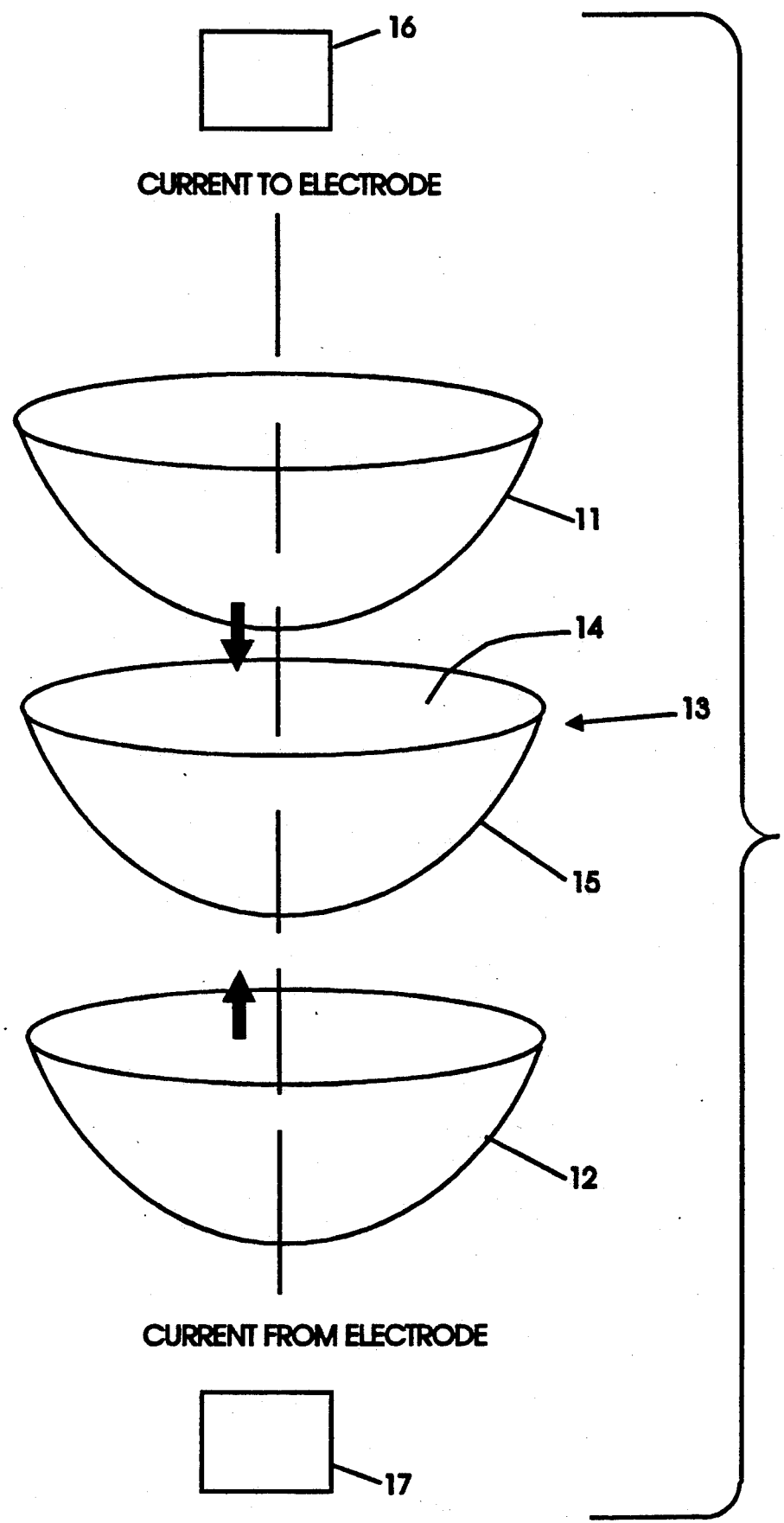
FIG. 1 is a schematic exploded view of a contact lens and adsorbent complex in which the adsorbent is contacted to both the concave and convex surfaces of the lens.

The present invention is directed at a method of removing contaminants from the surface and pores of contact lenses. The method comprises positioning the contact lens and an adsorbent so that the adsorbent is disposed between the contact lens and an electric current source, immersing the contact lens, adsorbent, and current source so disposed in a container which holds therein an aqueous saline solution, and applying an electric current from the source through the adsorbent and the lens so that contaminants carried by the lens migrate to the adsorbent.

This method relies on the principles of electroblotting, a process wherein electric current is applied to a substrate which contains ionic material. Individual charged molecules are attracted by and migrate to an electrode or other charged device. In the present invention, the materials removed by the current are proteins and other contaminants retained on contact lenses which, upon the application of current, migrate toward the electrically charged device. The contaminants are then trapped by an adsorbent having an affinity therefor which retains the contaminants. When the application of current ceases, the contaminant-laden adsorbent is removed. The cleaned lens is then ready for re-insertion by the wearer.

The method is suitable for use with any conventional contact lens that is capable of passing an electric current while immersed in saline solution. It is preferred that the lens be porous so that the saline solution in which the lens is immersed can flow into the interstices present in the lens and therefore pass current more easily. Suitable lenses include lenses which remain rigid when contacted with water (the two varieties of which are commonly known as "hard" contact lenses and as "gas-permeable" contact lenses), such as those formed from polymers of polymethylmethacrylate, silicone methacrylate, methacryloxyalkylsiloxane, methacrylopolysiloxane, methacrylate fluoropolymers, acrylamide, and copolymers thereof, and lenses which form a gel upon water absorption, (commonly known as "soft" lenses) such as those formed from hydroxyethyl methacrylate, vinyl pyrrolidone, cellulose acetate butyrate, and copolymers thereof. Lenses which are removed and cleaned daily and lenses which can be worn for weeks or longer between removal and cleaning are suitable.

The choice of adsorbent used to form the lens-adsorbent complex is not critical; any adsorbent to which protein and the other contaminants of a lens will adhere is suitable. Exemplary adsorbents include polymer membranes, such as PVDP, and cellulosic papers, such as nitrocellulose. Because generally the bulk of contaminants on a lens are proteins, it is preferred that the material comprising the adsorbent include a free chemical substituent which has a high affinity for protein, such as an amino, nitro, or carboxyl group. A preferred adsorbent is nitrocellulose membrane, available from Pharmacia Biotechnology, Piscataway, N.J.

Any configuration wherein the adsorbent is disposed between the lens and the electrically charged, device is suitable for use with the method. The adsorbent can be of any shape which permits it to be disposed between the electrically charged device and the lens. The adsorbent can be flat, folded, arcuate, or multi-arcuate; it can be circular, oval, elliptical, square, or any other polygonal shape. Direct contact of the adsorbent to the lens ensures that any contaminant migrating from the lens will immediately be trapped in the adsorbent and will not remain in solution, where potentially it could return to the lens surface; accordingly, it is preferred that the adsorbent is formed into an arcuate shape which is conformable to and matable with the arcuate shape of the contact lens. An adsorbent so shaped maximizes direct contact with the lens surfaces and therefore can entrap virtually all of the protein molecules migrating from the lens surface. Once trapped in the adsorbent, the adsorbed contaminants are unaffected by the equilibrium phenomenon created by the diffusion gradient and the electrochemical gradient described above, and thus are not free to return to the lens surface. Preferably, the adsorbent is sized to completely cover both the convex and the concave surfaces of the contact lens. This is shown in FIG. 1, wherein adsorbent cups 11 and 12 encapsulate lens 13, with adsorbent cup 11 nesting within the concave surface 14 of the lens 13 and adsorbent cup 12 covering convex surface 15 of the lens 13. As used herein, the "concave" surface of the lens is the surface that rests upon the cornea of the eye, and the "convex" surface of the lens is the surface that opposes the concave surface; i.e., it faces away from the cornea.

It is preferred that the adsorbent article be disposable. Disposability alleviates the need for cleaning the adsorbent after use. Further, the use of a new adsorbent unit with each cleaning minimizes the risk of contamination of the lens or infection to the wearer.

The choice of saline solution is not critical; any known saline solution for cleaning or soaking of contact lenses is suitable. Exemplary saline solutions can include boric acid, sodium borate, sodium chloride, sorbic acid, and edetate disodium. The pH of the saline solution should be adjusted so that it does not coincide with the isoelectric point of the protein contaminants; otherwise, the contaminants would have no electrical charge and thus would not migrate from the lens surface. It is also preferred that the saline solution be buffered to provide a constant pH solution; this ensures that such migrating proteins will maintain their charge during migration and therefore migrate reproducibly. The concentration of the solution is not critical; however, a dilute saline solution is preferred for rapid migration of contaminants, as an increased ionic concentration in the saline solution will provide additional ions which competitively carry electrical current with contaminant migrants.

The step of applying an electric current to the solution containing the lens can be carried out in any manner which causes current to pass through the lens itself. Generally, the current is supplied by electrodes immersed in the saline solution itself, but those skilled in this art will appreciate that any means of supplying current through the lens which causes the contaminants thereon to ionize and migrate to a charged device is suitable. When immersed electrodes are used, they are preferably placed so that the current flows through as much of the surface area of the lens as possible; in a preferred orientation, electrodes are placed on opposite sides of a lens so that current flowing between the electrodes flows substantially perpendicular to an axis extending through the diametric center of the lens and normal to the surface contour of the lens at that point. This configuration is seen in FIG. 1, wherein electrodes 16, 17 are seen on opposite sides of the complex formed by the lens 11 and the adsorbents 12, 13.

The amount of current directed through the lens can be any level which causes protein molecules to migrate toward the oppositely charged electrode. The amount can be direct current or alternating current. For convenience to the user, the current level should such that it can be provided by a household power source, such as a 120 volt electrical outlet, or by one or more household batteries. Also, the current level should be sufficiently high that substantially all of the protein migration occurs within a time period in which the wearer can conveniently function without wearing the lenses, such as overnight. A preferred current level which can satisfy these criteria is between about 0.1 and 200 milliamperes, with a more preferred current level being between about 10 and 100 milliamperes. It is also contemplated that the method may be used outside the home by commercial entities that would clean lens as the wearer waits; practice of the method in this fashion would require higher current levels, such as 300, 500, or even 1000 milliamperes, to reduce the cleaning duration sufficiently to be convenient for the consumer.

The present invention is better understood by the presentation of the following examples, which are not to be construed as limiting the scope of the invention, but instead are included to more completely illustrate the invention. In the examples, "°C" means degrees Centigrade, and "mA" means milliamperes.

EXAMPLE 1

Preparation of Contact Lenses for Protein Removal

Soft (hydrophilic) contact lens made by Barnes Hind of Sunnyvale, California were incubated for 7 days at 37° C. in one of three radio-labelled protein solutions: albumin; globulin; or lysozyme. These are proteins which make up the large majority of protein contaminants generally found on contact lenses. The proteins were obtained from Sigma Chemical Company, P.O. Box 14508, St. Louis, Mo. Proteins were radiolabeled with Iodine-125 (Amersham Corporation, 2636 South Clearbrook Drive, Arlington Heights, Ill.) according to the method described by M. A. K. Markwell, *Anal.*

Biochem. 125:427-432 (1982). After incubation, the radioactivity of the proteins was measured using a Packard Auto-Gamma Scintillation Spectrometer 5130 to provide an indication of the quantity of protein present in the lens. These lens were then cleaned by the procedures of Example 2 and comparative Example A to assess the cleaning capability of different cleaning methods.

EXAMPLE 2

Removal of Protein by Electroblotting of Complex

A lens prepared by the method of Example 1 was placed in a sandwich configuration between two sheets of nitrocellulose membrane (obtained from Pharmacia LKB Biotechnology) to form a lens-paper complex. The complex was then immersed in a bath containing Sensitive Eyes ™ saline solution obtained from Bausch & Lomb (Rochester, N.Y.). The nitrocellulose membrane was held in contact with the concave and convex surfaces of the lens by thermoplastic protrusions integral to the bath and its cover. The complex was retained in an orientation in which the concave surface faced upwardly and the convex surface faced downwardly. Two electrodes (Pharmacia LKB Biotechnology 2051 Midget Multiblot Electrophoretic Transfer Unit) connected to a power source (Pharmacia LKB Biotechnology 2103 Power Supply Pharmacia LKB Biotechnology) were immersed in the solution, one above the concave surface, and one beneath the convex surface, so that current would pass from an electrode through an adsorbent, then through the lens, and finally through the other adsorbent to the opposite electrode. The power source was activated and 50 mA of current was applied to the complex for 4 hours. The lens was then removed from solution for assessment of protein removal.

COMPARATIVE EXAMPLE A

Lenses prepared by the procedure of Example 1 were cleaned with (a) a commercial daily cleaner (Daily Cleaner, Eckerd Drug Company, Clearwater, Fla.); (b) Clensatron 700CL Automatic Contact Lens Cleaning Accessory, a detergent-based solution, (available from Questech International, Inc., Tampa, Fla.), in conjunction with Protein Remover Solution (Barnes-Hind, Sunnyvale, Calif.); and (c) Clensatron 700CL used with saline solution. In each instance the cleaning procedure used was that suggested by the manufacturer on the package.

After each lens was cleaned by these procedures or by the procedure of Example 2, the amount of protein removed was assessed by measuring the radioactivity of the proteins remaining on the lens. This was compared to the value measured prior to cleaning to obtain a percentage of protein removed.

Table 1 displays the results of the procedures.

TABLE 1

| Proteins | Electroblot (% removed) | Hand Wash (% removed) | Detergent-based Solution w/Protein Remover (% removed) | Detergent-based Solution w/Saline (% removed) |
| --- | --- | --- | --- | --- |
| Albumin | 95.32 | 95.39 | 96.33 | 91.10 |
| Albumin | 89.38 | 92.93 | 93.23 | 95.7 |
| Albumin | 97.08 | 93.98 | 87.58 | 95.01 |
| Globulin | 95.07 | 92.04 | 94.69 | 89.79 |
| Globulin | 96.17 | 90.29 | 94.48 | 81.28 |
| Globulin | 99.32 | 90.81 | 94.02 | 92.03 |
| Lysozyme | 98.54 | 87.18 | 88.31 | 83.29 |
| Lysozyme | 78.97 | 75.81 | 85.16 | 80.41 |
| Lysozyme | 99.98 | 63.41 | 65.47 | 59.88 |
| Average for all Proteins | 94.42 | 86.87 | 88.81 | 85.38 |

On average, the electroblotting technique of Example 2 removed a higher percentage of protein contaminants than did the other techniques.

The foregoing examples are illustrative of the present invention, and are not to be construed as limiting thereof. The invention is defined by the following claims, with equivalents of the claims to be included therein.

That which is claimed is:

1. A method of removing contaminants from a contact lens, comprising:
   (a) positioning the contact lens, a first adsorbent, and an electric current source configured so that said adsorbent is disposed between the contact lens and the electric current source and so that the current passes through said lens, said adsorbent including a free chemical substituent having a affinity for protein;
   (b) immersing the contact lens, the adsorbent, and the electric current source so disposed in a saline solution; and then
   (c) applying an electric current from the current source through the adsorbent and the contact lens so that contaminants carried by the contact lens migrate to the adsorbent.

2. A method according to claim 1, said contact lens having a concave surface and a convex surface, wherein said positioning step comprises contacting the concave surface of the lens to an adsorbent.

3. A method according to claim 1, said contact lens having a concave surface and a convex surface, wherein said positioning step comprises contacting the convex surface of the lens to an adsorbent.

4. A method according to claim 1, said contact lens having a concave surface and a convex surface, wherein said positioning step comprises contacting said concave surface to said first adsorbent and contacting said convex surface to a second adsorbent.

5. A method according to claim 1, wherein said positioning step comprises contacting the lens with an adsorbent article of arcuate shape conformable to and matable with an arcuate surface of the lens.

6. A method according to claim 1, wherein said contact lens is a porous contact lens.

7. A method according to claim 1, wherein the electric current is between about 0.1 and 200 milliamperes.

8. A method according to claim 1, wherein the electric current is between about 300 and 1000 milliamperes.

9. A method according to claim 1, wherein said applying step comprises applying an electric current so that proteins and fragments thereof migrate from the contact lens to the first adsorbent.

10. A method according to claim 9, wherein said applying step comprises applying electric current to the complex so that at least 90 percent of the proteins and fragments thereof migrate from said contact lens to the adsorbent.

11. A method of removing contaminants from a contact lens, comprising:
   (a) positioning the contact lens, a first adsorbent, and an electric current source configured so that said adsorbent is disposed between the contact lens and the electric current source and so that the current passes through said lens, said adsorbent being formed from a nitrocellulose membrane;
   (b) immersing the contact lens, the adsorbent, and the electric current source so disposed in a saline solution; and then
   (c) applying an electric current from the current source through the adsorbent and the contact lens so that contaminants carried by the contact lens migrate to the adsorbent.

12. A method according to claim 11, wherein said contact lens has a concave surface and a convex surface, and wherein said positioning step comprises contacting the concave surface of the lens to an adsorbent.

13. A method according to claim 11, wherein said contact lens has a concave surface and a convex surface, and wherein said positioning step comprises contacting the convex surface of the lens to an adsorbent.

14. A method according to claim 11, wherein said contact lens has a concave surface and a convex surface, and wherein said positioning step comprises contacting said concave surface to said first adsorbent and contacting said convex surface to a second absorbent.

15. A method according to claim 11, wherein said positioning step comprises contacting the lens with an adsorbent article of arcuate shape conformable to and matable with an arcuate surface of the lens.

16. A method according to claim 11, wherein said contact lens is a porous contact lens.

17. A method according to claim 11, wherein the electric current is between about 0.1 and 200 milliamperes.

18. A method according to claim 11, wherein the electric current is between about 300 and 1000 milliamperes.

19. A method according to claim 11, wherein said applying step comprises applying an electric current so that proteins and fragments thereof migrate from the contact lens to the first adsorbent.

20. A method according to claim 11, wherein said applying step comprises applying electric current to the complex so that at least 90 percent of the proteins and fragments thereof migrate from said contact lens to said absorbent.

* * * * *